(12) United States Patent
Stenzler

(10) Patent No.: US 7,108,666 B2
(45) Date of Patent: Sep. 19, 2006

(54) METHOD AND APPARATUS FOR PERFORMING A FORCED EXPIRATORY MANEUVER IN AN INFANT

(75) Inventor: Alex Stenzler, Long Beach, CA (US)

(73) Assignee: Sensormedics Corporation, Yorba Linda, CA (US)

( * ) Notice: Subject to any disclaimer, the term of this patent is extended or adjusted under 35 U.S.C. 154(b) by 558 days.

(21) Appl. No.: 10/338,188

(22) Filed: Jan. 7, 2003

(65) Prior Publication Data
US 2004/0129269 A1 Jul. 8, 2004

(51) Int. Cl.
A61H 31/00 (2006.01)
A61B 5/087 (2006.01)
A61M 16/00 (2006.01)
A62B 9/02 (2006.01)
A62B 18/02 (2006.01)

(52) U.S. Cl. .................. 601/44; 128/200.24; 600/532; 600/538

(58) Field of Classification Search ............ None
See application file for complete search history.

(56) References Cited

U.S. PATENT DOCUMENTS

| | | | |
|---|---|---|---|
| 1,055,267 A | 3/1913 | Gibson | |
| 2,364,602 A * | 12/1944 | Comer et al. ............... | 138/40 |
| 2,490,395 A | 12/1949 | Wilm ........................ | 128/30 |
| 2,833,275 A | 5/1958 | Tunnicliffe ............... | 128/30 |
| 2,869,537 A | 1/1959 | Chu .......................... | 128/27 |
| 3,042,024 A | 7/1962 | Mendelson ................ | 128/30 |
| 3,043,292 A | 7/1962 | Mendelson ................ | 128/30 |
| 3,481,327 A | 12/1969 | Drennen .................... | 128/30.2 |
| 3,509,899 A * | 5/1970 | Hewson .................... | 137/87.04 |
| 3,621,835 A | 11/1971 | Suzuki et al. ............. | 128/2.08 |
| 3,786,809 A | 1/1974 | Kitrilakis ................. | 128/191 |
| 4,004,579 A | 1/1977 | Dedo ........................ | 128/28 |
| 4,539,984 A | 9/1985 | Kiszel et al. ............. | 128/204.23 |
| 4,977,889 A | 12/1990 | Budd ........................ | 128/30.2 |
| 5,222,478 A | 6/1993 | Scarberry et al. ......... | 128/30.2 |
| 5,261,397 A | 11/1993 | Grunstein ................ | 128/204.18 |
| 5,318,038 A | 6/1994 | Jackson et al. ........... | 128/720 |
| 5,513,647 A | 5/1996 | Castile .................... | 128/720 |

(Continued)

OTHER PUBLICATIONS

Adler, S.M. et al., "Flow-Volume Relationship At Low Lung Volumes In Healthy Term Newborn Infants," Pediatrics, vol. 61, No. 4, pp. 636-640, Apr. 1978.

(Continued)

Primary Examiner—Glenn K. Dawson
(74) Attorney, Agent, or Firm—Sidley Austin LLP

(57) ABSTRACT

Disclosed is a method and device for performing forced expiratory maneuver in an infant to assess the infant's pulmonary function. Under this method, the infant's lungs are synchronously inflated to super-atmospheric levels synchronous with the infant's natural tidal inspiration for a plurality of consecutive respiratory cycles. The end-expiratory $CO_2$ levels in the infant's respiration are measured during the test. When the end-expiratory $CO_2$ concentration decreases from the baseline by a pre-defined amount, the infant lungs are rapidly inflated to substantially total lung volume and rapidly deflated to produce a maximum forced expiration. The pre-defined amount of change in $CO_2$ concentration is usually determined by the testing clinician. Typical concentration drop in $CO_2$ levels, for example, ranges between 4 and 8 mmHg. But the decrease may also be as little as 2 mmHg or as much as 15 mmHg, depending on the testing clinician. The decrease in the end-expiratory $CO_2$ level of the infant indicates that the infant's respiratory center is sufficiently modified to allow for the measurement.

12 Claims, 3 Drawing Sheets

U.S. PATENT DOCUMENTS 6,090,056 A * 7/2000 Bystrom et al. .............. 601/41
6,581,595 B1 * 6/2003 Murdock et al. ...... 128/204.18

OTHER PUBLICATIONS

Amsler, B. et al., "The Effects Of Varying Inflation And Deflation Pressures On The Expiratory Deflation Flow-Volume Relationships In Anaesthetized Rhesus Monkeys," British Physio. Society.

Bar-Yishay et al., "Partial Forced Expired Flow-Volume (PEFV) Maneuvers By The Squeeze Technique Does Not Yield Higher Flows With Better Infant Relaxation," Am Rev Respir Dis, vol. 143, No. 4, Part 2 (Suppl.), Apr. 1991.

Deakers, T.W. et al., "Demonstration Of Flow Limitation During Maximum Expiratory Deflation Flow-Volume Maneuvers In Anesthetized Rhesus Monkeys," Am Rev Respir Dis, vol. 143, No. 4, Part 2 (Suppl.), Apr. 1991.

Hammer, J. et al., "The Achievement Of Flow Limitation In Intubated Infants With Normal Lungs And Obstructive Airways Disease," Am Rev Respir Dis, vol. 147, No. 4, Part 2 (Suppl.), Apr. 1993.

Hammer, J. et al., "Effect of Lung Volume on Forced Expiratory Flows During Rapid Thoracoabdominable Compression in Infants," J. Appl. Physiol. 78, vol. 5, pp. 1993-1997 (1995).

Hammer, J. et al., "Flow Limitation In Anesthetized Rhesus Monkeys: A Comparison Of Rapid Thoracoabdominal Compression And Forced Deflation Techniques," Pediat. Res., vol. 39, No. 3, pp. 539-546 (1996).

Inscore, S.C. et al., "Non-Invasive Measurement Of The Passive Deflation Compliance Of The Respiratory System In Infants," Am Rev Respir Dis, vol. 135, No. 4, Part 2 (Suppl.), Apr. 1987.

LeSouef, P.N. et al., "Forced Epiratory Maneuvers," Infant Respiratory Function Testing, Chapter 15, pp. 379-408 ( p. 390 of article only) (1996).

Motoyama, E.K., "Pulmonary Mechanics During Early Postnatal Years," Pediat. Res., vol. 11, pp. 220-223 (1977).

Motoyama et al., "Early Onset Of Airway Reactivity In Premature Infants With Bronchopulmonary Dysplasia," Am Rev Respir Dis, vol. 136, pp. 50-57 (1987).

Newth et al., "The Effects Of Varying Inflation And Deflation Pressures On The Maximal Expiratory Deflation Flow-Volume Relationship In Anesthetized Rhesus Monkeys," Am Rev Respir Dis, vol. 144, pp. 807-813 (1991).

Newth et al., "The Achievement Of Flow Limitation In Anesthetized Rhesus Monkeys: A Comparison Of Squeeze Jacket And Deflation Techniques," Am Rev Respir Dis, vol. 145, No. 4, Part 2 (Suppl.), Apr. 1992.

Pedersen et al., "Airway Compliance And Flow Limitation During Forced Expiration In Dogs," J. Appl. Physiol., vol. 52, No. 2, pp. 357-369 (1982).

Tepper et al., "Comparison Of Forced Expiratory Flows Initiated At End-Tidal Inspiration And At Elevated Lung Volumes In Normal Infants," Am Rev Respir Dis, vol. 147, No. 4, Part 2 (Suppl.), Apr. 1993.

Turner D.J. et al, "Assessment of Respiratory Function in Infants Pumped to Higher Lung Volumes," Am. Rev. of Respiratory Disease, vol. 143, p. 126 (abstract), Apr. 1991.

Turner D.J. et al., "Assessment of Forced Expiratory Volume—Time Parameters in Detecting Histamine-Induced Bronchoconstriction in Wheezy Infants," Abstract, Am Rev of Respiratory Disease, vol. 147, No. 4, Part 2, Apr. 1993.

Turner, D.J. et al., "Pressure Transmission Across The Respiratory System At Raised Lung Volumes In Infants," Am Rev Respir Dis, vol. 145, No. 4, Part 2 (Suppl.), Apr. 1992.

Turner, D.J. et al., "Respiratory Function From Raised Lung Volumes In Normal And Wheezy Infants," Am Rev Respir Dis, vol. 145, No. 4, Part 2 (Suppl.), Apr. 1992.

Turner, D.J. et al., "Improved Detection Of Abnormal Respiratory Function Using Forced Expiration From Raised Lung Volumes In Infants With Cystic Fibrosis," Am Rev Respir Dis, vol. 147, No. 4, Part 2 (Suppl.), Apr. 1993.

ECO Medics Operating Guide for Exhalyzer D, Oct. 2001.

ECO Medics Exhalyzer®D Specifications.

ECO Physics spiroWare® "Add on Tools", Eco Physics Website Sep. 30, 2002.

ECO Physics Scientific Articles, Eco Physics Website Sep. 30, 2002.

Equilibrated Bio Systems, Inc., 2605 Infant Hugger Operator's Manual.

Equilibrated Bio Systems, Inc., Introducing the EBS2605 Infant Hugger.

SensorMedics 2600 Pediatric Pulmonary Cart.

* cited by examiner

METHOD AND APPARATUS FOR PERFORMING A FORCED EXPIRATORY MANEUVER IN AN INFANT

FIELD OF THE INVENTION

The field of the present invention relates to measurements of pulmonary function in infants and more particularly to forced expiratory tests in infants.

BACKGROUND OF THE INVENTION

Forced expiration is a simple yet useful test for pulmonary function. In this test, the patient makes a maximum inspiration, filling the lungs to their maximum volume known as Total Lung Capacity (TLC), and immediately expels the inhaled air as rapidly as possible to empty the lungs to the minimum volume attainable by this maneuver. By measuring the volume rate of expiration and the total amount of air expired over time, a number of parameters can be used as indications of pulmonary function and health. Examples of these parameters include the forced expiratory flow in the first second of the forced expiration ($FEV_1$), the expiratory flow rate averaged over the period from a volume of 25% to 75% of the total expired air volume ($FEV_{25-75}$), the total volume of expired air (FVC) plotted against the flow rate. The forced expiration test is useful for quantitating levels of dysfunction occurring in relation to both obstructive and restrictive pulmonary processes.

In infants, lung function tests that evaluate airway function is particularly difficult as they cannot cooperate for the test. Unlike an older child or an adult, an infant cannot be expected to voluntarily perform the forced expiration on his own. Hence, to acquire data on an infant's airways, clinicians have developed techniques such as the "squeeze" or "hug" technique. In this method, an inflatable vest or jacket is wrapped around the infant's chest and abdomen. The vest is attached to a pressurized reservoir with a valve controlling the flow of air from the reservoir into the vest. With the reservoir, the vest can be rapidly filled with air (to varying pressures) to squeeze the infant's body within the vest and expel the air from the infant's lungs so as to replicate the forced flow procedure. Because these squeezes are made from end-tidal inspiration, the infant is not inflated to TLC before the squeeze resulting in partial respiratory curves.

One way to acquire more information across a greater exhale volume of the infant is to inflate the infant's lung to a higher lung volume before performing the squeeze. For example, infant lungs can be inflated to +15 to +50 cm $H_2O$ before squeezing or deflation that forces the air out. See e.g., Motoyama, E K, *Pulmonary Mechanics During Early Post Natal Years*, Pediatric Respiration, Vol. 11, 1977, pp. 220–223; Turner, D J et al., *Assessment of Forced Expiratory Volume-Time Parameters In Detecting Histamine Induced Bronchoconstriction in Wheezy Infants*, Pediatric Pulmonology, Vol. 15, No. 4, pp. 220–4, April 1993; Hammer J. and Newth, C J., *Effect of Lung Volume on Forced Expiratory Flows during Rapid Thoracoabdomical Compression in Infants*, Journal of Applied Physiology, Vol. 78, No. 5, 1995, pp. 1993–1997; Newth, C J et al., *The Effects of Varying Inflation and Deflation Pressures on the Maximal Expiratory Deflation Flow-Volume Relationship in Anesthetized Rhesus Monkeys*, American Review of Respiratory Disease, Vol. 144, No. 4, pp. 807–13, October 1991. Lung volume may also be increased by providing for multiple inspiration without exhalation. Because under these methods, more air is expelled than during a normal breath, the time for exhalation is prolonged beyond what the infant's brain determines the time should be. In response to the innate timing cycle, however, the infants frequently begin inspiration before the forced maneuver is completed, and invalidates the data.

One way to address this problem was for the physician to wait until a respiratory pause has been achieved in the infant before "squeezing" or forcing the infant to exhale. In this method, the physician first inflates the infant's lung synchronously with the infant's natural tidal inspiration to a lung volume greater than the lung volume reached with natural breathing for several breaths. Inflating the infant's lungs in this way will cause a few seconds of pause in the infant's breathing. During this pause period, the infant's lung is again rapidly inflated and immediately afterwards, the chest and abdomen is "squeezed" to produce a maximum forced expiration. In the above method, however, the infant's carbon dioxide levels in the blood, which controls their innate respiratory timing, will be returning to normal while the clinician is waiting to determine if there has been a respiratory pause. Carbon dioxide levels returning to normal may affect the test results. Accordingly, there is a continuing need for new methods of performing forced expiratory maneuvers in infants.

SUMMARY OF THE INVENTION

The present invention is directed to an improved method and a device for testing lung function in infants using the forced expiratory maneuver. In one aspect of the invention, the improved method comprises the steps of inflating the lungs of the infant with air synchronously with the infant's natural tidal inspiration for a plurality of consecutive respiratory cycles and monitoring the end-expiratory carbon dioxide ("$CO_2$") levels in the infant's respiration during the test. When the end-expiratory $CO_2$ concentration decreases from baseline by a pre-defined amount, the infant lungs are rapidly inflated to substantially total lung volume and are immediately deflated either by compressing the infant's chest and abdomen or by sucking the air out of the lungs using a negative pressure reservoir such as a vacuum source. The pre-defined amount of change in $CO_2$ concentration is usually determined by the testing clinician. Typical concentration drop in $CO_2$ levels, for example, ranges between 4 and 8 mmHg. But the decrease may also be as little as 2 mmHg or as much as 15 mmHg, depending on the testing clinician. The decrease in the end-expiratory $CO_2$ level of the infant indicates that the infant's respiratory center is sufficiently modified to allow for the measurement.

The advantage of monitoring the end-expiratory $CO_2$ levels over the method of waiting for a pause in the infant's breathing before performing the squeeze is that in the latter method, the infant's body continually produces carbon dioxide during the pause. As mentioned before, while the clinician is waiting to determine if there has been a respiratory pause by the infant, the infant's carbon dioxide levels in the blood will be returning to normal. Monitoring of the end-expiratory $CO_2$ levels, instead, does not require waiting for a pause, provides an immediate signal that the infant lungs can be inflated and deflated, and ensures that the carbon dioxide levels do not rise too much as to affect the result of the tests. Furthermore, monitoring the end-expiratory $CO_2$ levels also ensures that carbon dioxide levels are not overly reduced by over ventilation. Over reduction of carbon dioxide levels may be associated with reduction of cerebral blood flow and can potentially be associated with neurological injury. Thus, the present method limits the risk in over reduction in carbon dioxide and also allows for the determination of the optimal time to perform the compression without the need to observe the respiratory effort of the infant for an extended period of time.

In another aspect of the invention, an apparatus is provided to perform a forced expiratory maneuver in an infant. The apparatus generally comprises a mask connected to a source of breathable air, a flow sensor, a $CO_2$ sensor, and a lung deflation means under the control of a controller. Example of the lung deflation means include, but is not limited to an inflatable vest that compresses the infant's thoracic-abdominal region and a negative pressure reservoir that sucks the air from the infant's lungs. In a preferred embodiment, the controller is configured to receive signals from the flow sensor and $CO_2$ sensor. When the concentration of $CO_2$ detected by the $CO_2$ sensor equals a pre-defined concentration, the controller commands inflation of the infant's lungs to total lung capacity (TLC), followed by the rapid deflation of the infant's lungs to expel substantially all of the air in the lungs.

These and other features and advantages of the preferred embodiment will be described below in conjunction with the figures.

DETAILED DESCRIPTION OF THE PREFERRED EMBODIMENTS

Figure 1:
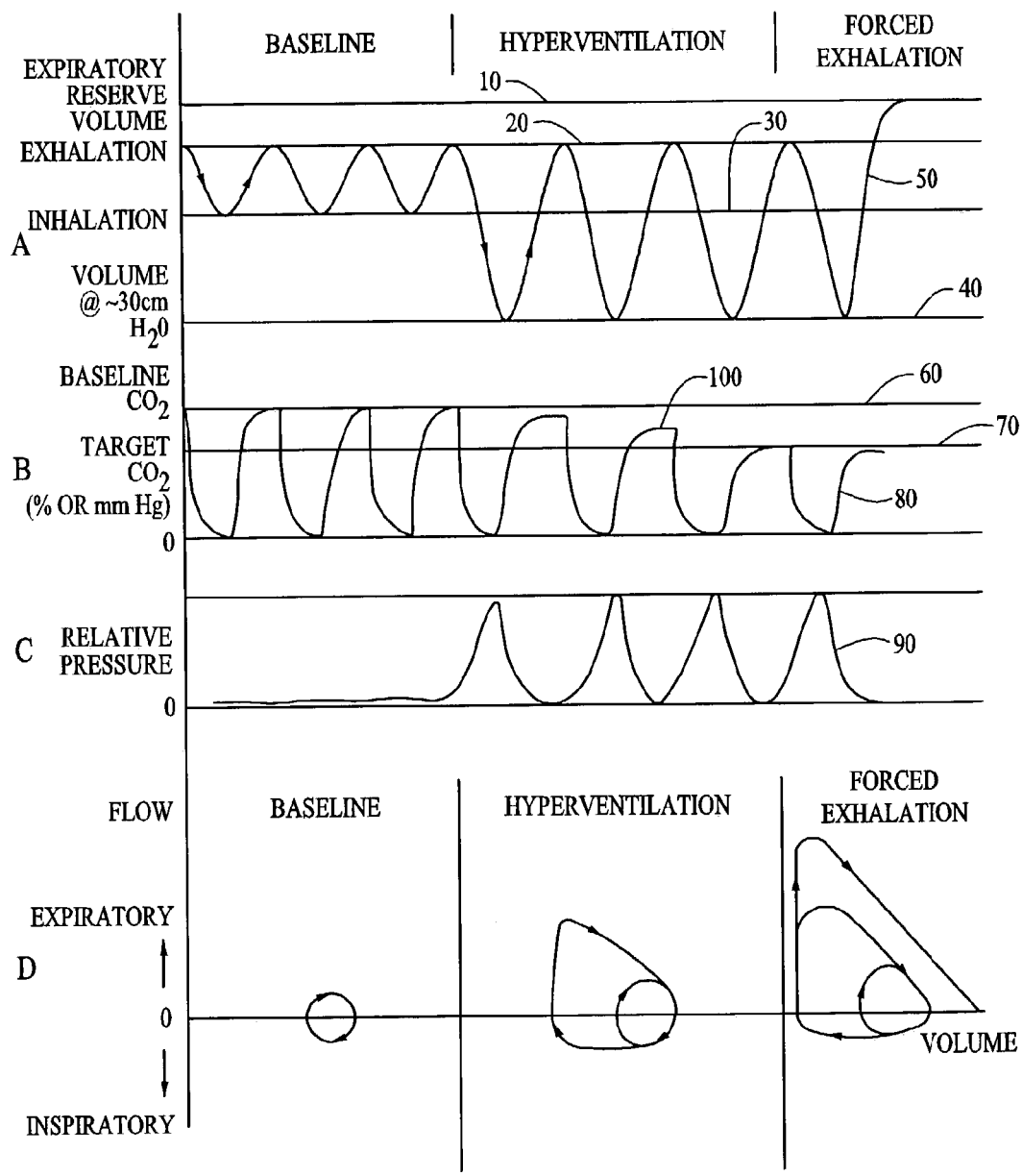
FIG. 1, panel A is a plot showing the spirometric lung volumes versus time for an infant undergoing the procedure according to one embodiment of the invention. Panel B is a plot showing the $CO_2$ levels of the infant corresponding in time to the lung volume of panel A. Panel C is a plot of air pressure delivered synchronously with the infant's tidal volume to hyperventilate the infant. Panel D is a flow/volume loop plot corresponding in time to the lung volume in panel A.

FIG. 1 illustrates the breathing pattern of an infant undergoing the forced expiration maneuver procedure according to one embodiment of the invention, wherein the relevant events are indicated by the three traces 50, 80, and 90. In panel A, changes of lung volume versus time is illustrated. The vertical axis in panel A represents the relative lung volume as measured by the volume of air inspired and expired. Of the total lung capacity (TLC), an expiratory reserve volume is represented by the space between lines 10 and 20 at the top portion of the plot. The expiratory reserve volume (ERV) is the portion of the lung volume that is not emptied during normal tidal exhalation by the infant. Below the expiratory reserve volume is the tidal volume, which represents the portion of the lung volume that is exchanged during natural breathing. The tidal volume is represented in the plot as the space between lines 20 and 30. The portion of the lung that is inflated above the natural tidal volume, i.e., the inspiratory reserve volume (IRV), is shown at the bottom part of panel A as the space between lines 30 and 40. The horizontal axis of the plot represents time, with the three relevant time periods delineated in the plot as "Baseline," "Hyperventilation," and "Forced Exhalation." The trace 50 represents the amount or volume of air inhaled and expired by the infant at a given time. The volume of air expired or inspired may be monitored usually by flow sensor such as an ultrasonic flow sensor, a pneumotachograph, or any other device that measures the flow rate of the gas inspired or expired. Calculations of volume can then be obtained by integrating the flow rate over time. To measure flow rate, a flow sensor may also, for example, use a flow-resistant element that measures pressure drops or a small heated mass that respond to cooling in that current required to maintain the temperature is proportional to the air flow. Examples of commercially available flow sensors are SensorMedics Corporation's (Yorba Linda, Calif.) Mass Flow Sensor, Hans Rudolph's (Kansas City, Mo.) Pneumotachograph, and Erich Jaeger's (Hoechburg, Germany) Screen Pneumotachograph.

In panel B, the $CO_2$ level versus time of the infant undergoing this procedure is illustrated. The vertical axis represents $CO_2$ concentration of the expired breath from the infant. The baseline $CO_2$ concentration, represented by line 60, is the concentration of $CO_2$ at end-tidal expiration during natural breathing by the infant. Concentration of $CO_2$ may be expressed in percent, torr, or mmHg. Measurement of end-tidal $CO_2$ concentration may be achieved by a $CO_2$ sensor. An example of a $CO_2$ sensor may be a rapid-response Non-Dispersive Infrared (NDIR) sensor, which works by directing a beam of infrared light through a sample of gas and measuring the amount of infrared energy that is being absorbed. Carbon dioxide sensors are also commercially available, for example, from SensorMedics Corporation (Yorba Linda, Calif.) with its Vmax29 and Vmax 26 products.

Panel C illustrates the pattern at which breathable air at super-atmospheric pressure is provided to the infant to inflate the infant's lungs synchronously with the infant's natural breathing. The trace 90 represents the air pressure that is applied at the mouth and nose of the infant synchronously with the infant's natural tidal breathing. The vertical axis of panel C represents relative pressure. Panel D is an alternative representation of the respiratory volume during expiration and inspiration at the three different stages of the procedure. The horizontal axis represents the volume of air traveling in and out of the lungs as depicted by the arrows. The vertical axis above the horizontal axis represents flow of air during expiration and the vertical axis below the horizontal axis represents flow of air during inspiration.

In performing the forced expiration maneuver, the infant is first fitted with a mask that preferably covers his nose and mouth. A compression device such as an inflatable vest is also fitted on the infant's thoracic-abdominal region. Preferably, the mask is connected to an air supply that can be delivered at super-atmospheric pressure and can be controlled by the clinician. To minimize leakage, seal around the mask can be achieved using elastic straps around the infant's head and/or medical putty applied around the edges of the mask, or the mask can be hand held to the infant's face. A flow sensor is placed in the air conduit to the mask to measure the airflow in and out of the infant's lungs for determining the flow rates and lung volumes, and to provide a control signal when the method is performed under automatic control. A $CO_2$ sensor is also placed in the air conduit of the mask to measure the amount of $CO_2$ during expiration and to provide a control signal when the method is performed under automatic control. Once the devices are in place, the infant is allowed to breathe naturally as seen in the "baseline" period of panel A. The $CO_2$ concentration is monitored during this period to establish a baseline level for the $CO_2$. The physician or testing clinician may then select a pre-defined decrease in $CO_2$ level upon which the compression of the infant's chest is to be performed.

To reduce the $CO_2$ level to the target concentration, the infant lungs are inflated with extra air synchronously with its natural breathing rhythm by applying an air pressure in the range of about 15 cm $H_2O$ to about 50 cm $H_2O$, preferably about 30 cm $H_2O$ to 40 cm $H_2O$, to the mask, as seen in the hyperventilation period depicted in FIG. 1. Peak 100 in panel B, for example, represents the drop in $CO_2$ level as the infant is hyperventilated with supra-atmospheric air. As successive hyperventilation occurs, the $CO_2$ level eventually reaches the pre-defined target level (line 70). At which time, a final hyperventilation or inflation of the infant lungs at super-atmospheric pressure is performed, and the compression device is activated to squeeze around the infant's chest and to force expiration of substantial all of the air in the infant lungs, including the expiratory reserve volume. The amount of pressure applied around the infant's chest may be determined and set by the testing clinician, but the typical range is about 40 cm of water to about 100 cm of water, and preferably about 60 cm of water to about 80 cm of water.

When the forced expiratory maneuver is complete, as indicated by the cessation of outflow measured by the flow sensor, the pressure around the infant's chest is immediately released, and the infant returns to normal tidal breathing. A preferred time to perform this artificial inspiration and force expiration maneuver is when the infant is sleeping or under sedation so that the infant will better tolerate the maneuver.

Figure 2:
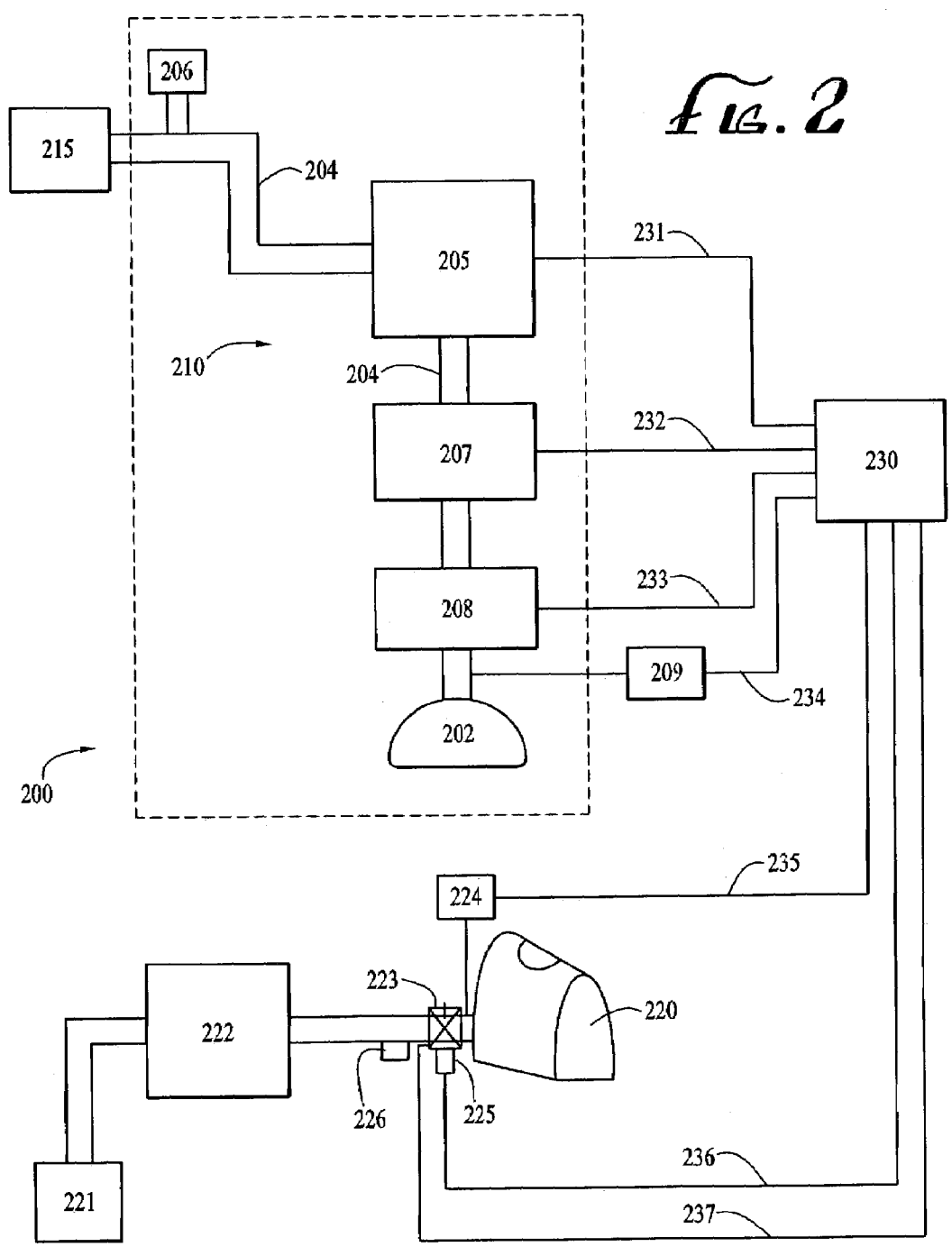
FIG. 2 is a schematic diagram of an apparatus for performing the forced expiration maneuver according to one embodiment of the present invention.

To perform the forced expiration maneuver described above, an apparatus suitable for this method is illustrated in FIG. 2. The apparatus 200 in FIG. 2 is depicted schematically for purposes of showing the connection and operation of the parts of the apparatus and should not be interpreted as limiting the particular location or distance of the parts relative to each other. Generally, the apparatus includes an air distribution manifold 210, a source of breathable air 215, an inflatable vest 220, and a controller 230.

Still referring to FIG. 2, the air distribution manifold 210 may include a patient interface device, preferably a mask 202 adapted to be fitted over the infant's nose and mouth and wherein the mask is connected to a source of breathable air 215 via an air conduit 204. Alternatively, the mask 202 can also be a nasal mask which covers and is sealed to the infant's face around the nose. In intubated infants, for example, the patient interface device may include a tubing for inserting into the infant's airway. The source of breathable air 215 can be in any form capable of providing a pressure at the infant's mouth and/or nose sufficient for inflation of the infant's lungs to full capacity. Examples of the source can be an air blower, a pressurized air cylinder or a dedicated line in a medical facility having a pre-set oxygen concentration. In practice, a pressure of about 30 cm of water is adequate, but other pressures may also be used. The air conduit 204 acts as a supply line from the source of breathable air 215 to the mask 202. The air conduit 204 may comprise a control valve 205 that allows super-atmospheric air to be delivered to the mask 202. The control valve 205 may be any valve known in the art that opens to allow gas to enter from the source of breathable air 215 to the mask 202. In one embodiment, the control valve 205 may further allow air to enter from, and exit to, the atmosphere and may close to prevent flow of gas in and out of the atmosphere. In this embodiment, when the control valve 205 is closed to the atmosphere, for example, breathable air from the source 215 may flow through the control valve 205 to the mask 202. Since air cannot exit to the atmosphere, pressure builds up in the air distribution manifold 210. A pop-off valve 206 or any other pressure limiting valve may also be included and provided along the air conduit such that when a maximum pressure is reached within the air distribution manifold 210, the pop-off 206 valve opens and air is released while maintaining the desired pressure.

Figure 3:
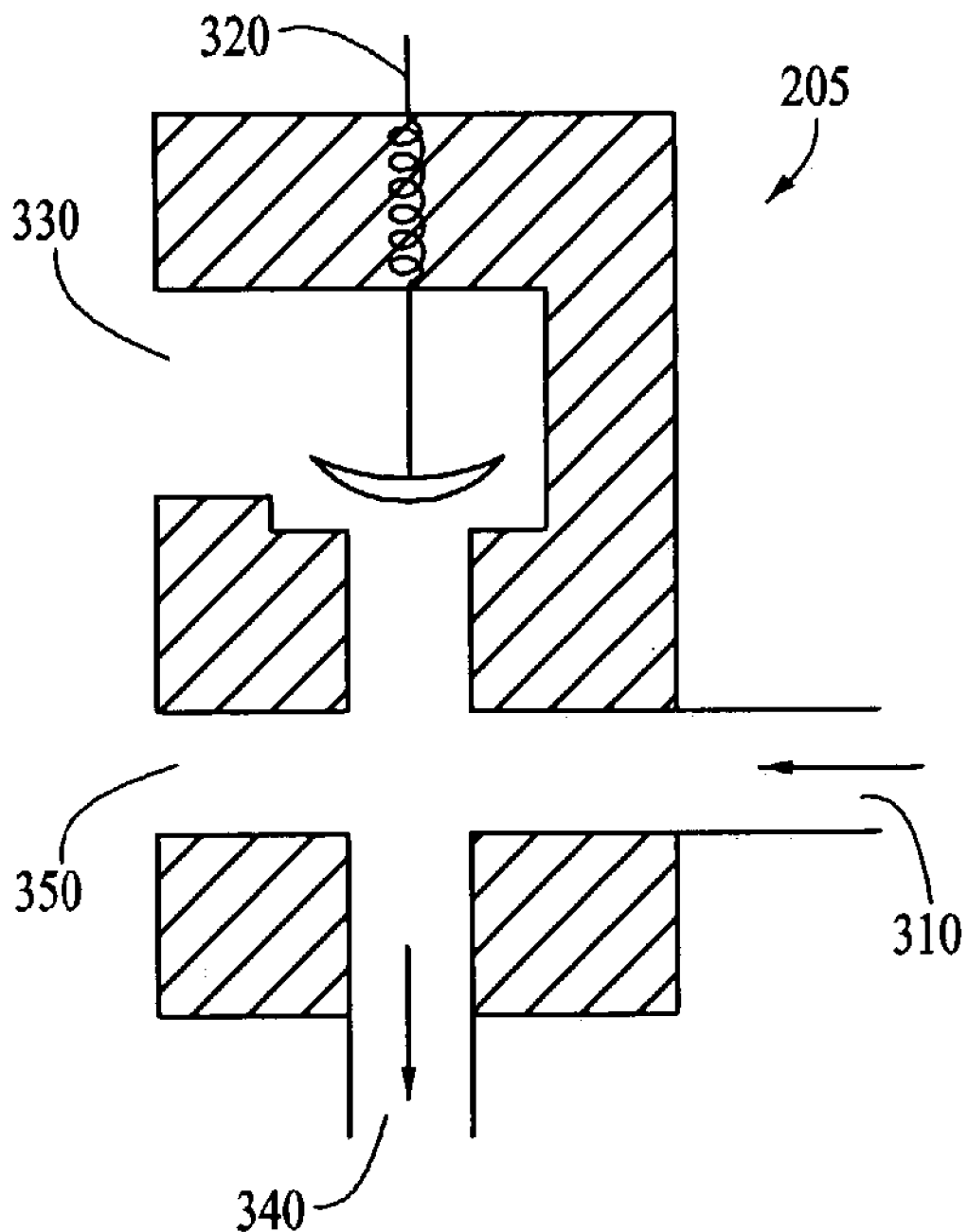
FIG. 3 is an example of a control valve 205 of the apparatus 200 represented in FIG. 2.

In a preferred embodiment, the control valve 205 is configured as shown in FIG. 3. In this embodiment, air from the source 215 flows into the control valve 205 through an inlet port 310. The control valve 205 may comprise a controllable spring valve 320 or any other suitable device for regulating the flow of gases or air. When the spring valve 320 is closed, the exhaust port 330 to the atmosphere is blocked. Thus, air can travel only to the supply port 340 leading to the mask 202. When the spring valve 320 is opened, air can freely flow in and out of the exhaust port 330. The spring valve 320 may be automatically controlled by the controller 230 or manually controlled by an operator. Although the control valve 205 is described in this embodiment as having a spring valve 320, other types of valves commonly used in the art may also be used to regulate the flow of gases or air. Examples of these other types of valves include Hans Rudolph's (Kansas City, Mo.) manual or pneumatic valves. In another embodiment, the control valve 205 may further include a safety port 350. Flow of gas in and out of the safety port 350 may be regulated by a manual release valve (not shown) or by the finger of an operator. For example, the safety port 350 may be obstructed by the operator's finger during pressure buildup within the air distribution manifold. In an emergency when the automatic spring valve 320 fails or when pressure needs to be otherwise released from the air distribution manifold 210, the operator merely removes his finger to release the pressure.

Referring back to FIG. 2, to determine the flow of gases, a flow sensor 207 (such as an ultrasonic flow sensor or a pneumotachograph) is provided along the air conduit 204 and is in fluid communication with the mask 202. A flow signal line 232 also connects the flow sensor 207 to the controller 230 such that signals representing the flow rate measured by the flow sensor is transmitted to the controller 230 via the flow signal line 232. A $CO_2$ sensor 208 for measuring the end-expiratory $CO_2$ concentration is also provided along the air conduit 204 and in fluid communication with the mask 202. Similar to the flow sensor 207, a $CO_2$ signal line 233 also connects the $CO_2$ sensor 208 to the controller 230 such that signals representing the $CO_2$ concentration measured by the $CO_2$ sensor 208 is, transmitted to the controller 230 via the $CO_2$ signal line 233. A pressure sensor 209 that measures the pressure delivered to the mask 202 may also be provided and is connected to the controller via the pressure signal line 234. The above signal lines may employ direct electrical connections, fiber optic cables, or even radio frequency or infrared radiation signaling.

In order to compress the infant's lungs to produce the forced expiratory maneuver, the infant may be fitted with an inflatable vest 220. Inflatable vests suitable for use with the apparatus 200 are available in several designs. The inflatable vest may be pneumatically, hydraulically, mechanically, or electrically operated. Inflatable vest are also commercially available from, for example, Consulting Western Services (Lakewood, Calif.) or Hammersmith Hospital (UK). In a pneumatically operated vest, for example, the inflatable vest 220, as shown in FIG. 2, is typically connected to a reservoir 222 containing air or any other gas at super-atmospheric pressure. The reservoir 222 may be a stand alone pressurized cylinder containing gas, which are known in the art or it may be connected to another air source 221 that feeds into the reservoir 222. Gas in the reservoir 222 may be released or regulated by an inflation valve 223, which can be controlled by the controller 230 through the inflation valve signal line 237. Along the connection between the reservoir 222 and the inflatable vest 220 may also be provided a vest pressure sensor 224, a vest vent 225, and a safety pop-off valve 226. Although the inflation valve 223 and the vest vent 225 are depicted separately in FIG. 2, these two structures can also be combined into a single unit as when a switching type valve is used. For example, in a switching type valve, inflation of the vest 220 is achieved by the valve switching to a first position that allows the gas to flow from the reservoir 222 to the inflatable vest 220 and wherein the vest vent is closed. When the vest 220 is to be deflated, the switching type valve switches to its exhaust position wherein the vest vent is opened and gas flow from the reservoir 222 is blocked. Switching type valves are commercially available from, for example, Consulting Western Services (Lakewood, Calif.) or Hans Rudolph's (Kansas City, Mo.).

To provide for automatic or semi-automatic operation, a controller 230 may be used to control the apparatus 200. The controller 230 is preferably a digital computer or other electronic device having a digital processor. Instructions for the controller 230 can be stored in read-only-memory (ROM), logic circuit, or through software programming stored in RAM, hard disk, CD-ROM, diskette, or any other storage medium. A keyboard, mouse, light pen, or any other interface device used with a monitor display may be used by the operator to interact with the controller 230. Preferably, the controller 230 includes a memory (e.g., RAM, hard drive, etc.) or any other data recorder for recording data received from the flow sensor 207, $CO_2$ sensor 208, pressure sensor 209, or vest pressure sensor 224. While a digital computer is preferred, it is also contemplated that analog switching devices known in the art may also be used to control the apparatus 200. Furthermore, although the controller 230 is shown as a single unit in FIG. 2, it is also contemplated that controller 230 may be comprised of multiple units in communication with each other. For example, a vest control unit for controlling the inflation and deflation of the vest 220 and receiving signals from the vest pressure sensor 224 may be a separate unit from the control unit that controls the inflation of the infant's lungs and that receives signal from the flow sensor 207, the $CO_2$ sensor 208, and the pressure sensor 209.

The operation of the apparatus 200 will now be described. At the beginning of the forced expiratory procedure, the control valve 205 is opened freely to the atmosphere. Air flows from the source 215 through the air conduit 204, control valve 205, flow sensor 207, and $CO_2$ sensor 208 to the mask 202 during inspiration, and expired air from the mask 202 is exhausted to the atmosphere through the exhaust port 330 (FIG. 3) of the control valve 205 or the safety port 350 (FIG. 3). With the air freely flowing, the infant can breathe naturally by inhaling and exhaling through the flow sensor 207, $CO_2$ sensor 208, and the control valve 205. The flow sensor 207 measures the inflow and outflow of air as the infant breathes and provides a signal through the flow signal line 232 to the controller 230. The $CO_2$ sensor also measures the base line $CO_2$ concentration at this stage and provides a signal through the $CO_2$ signal line 233 to the controller 230. To raise the lung volume of the infant, an operator activates the apparatus 200 through the controller 230, for example, by pressing a system foot-switch, a keyboard, a start button, or hand switch. The controller 230 then commands the control valve 205 to shut off flow in and out of the atmosphere, for example, by closing the spring valve 320 (FIG. 3). The command signal to the control valve 205 from the controller 230 may be transmitted through the control valve signal line 231. When equipped with a safety port 350, the operator also obstructs the safety port 350 by closing a manual release valve or by placing a finger over the safety port 350. Once the control valve 205 and the safety port 350 are closed to the atmosphere, the air flowing into the control valve 205 can only flow to the mask 202 until the pressure measured at the airway opening reaches a preset value (such as 30 cm $H_2O$). The preset value may be determined by setting the pop-off valve 206 to the desired pressure so that when the pressure is reached, the pop-off valve 206 opens.

Once the flow to the infant ceases as measured by zero inspiratory flow through the flow sensor 207, the controller 230 then sends a signal over the control valve signal line 231 commanding the control valve 205 to open to the atmosphere (for example, by opening the spring valve 320) and to release the air in the infant's lungs to the atmosphere. $CO_2$ concentration is also monitored at the infant's airway opening during this phase and is compared to the base line $CO_2$ concentration or a target $CO_2$ concentration. If the $CO_2$ concentration has not reached the target level or has not decreased from the baseline by a pre-defined amount, then the controller 230 sends a signal through the control valve signal line 231 to command closure of the control valve 205 once the expiratory flow from the infant ceases (as measured by zero expiratory flow through the flow sensor 207.) Inhalation at super-atmospheric pressure and exhalation as described above are repeated until the $CO_2$ concentration reached the target level or has been reduced from the base line $CO_2$ concentration by a predefined amount. The target $CO_2$ concentration may be set by the attending operator as a function of the base line $CO_2$ concentration. For example, the target $CO_2$ concentration may be derived by subtracting from the base line $CO_2$ concentration a pre-defined amount. The pre-defined decrease in $CO_2$ concentration is typically in the range of 4 and 8 mmHg, but may also be as little as 2 mmHg or as much as 15 mmHg. Alternatively, the target $CO_2$ concentration may also be set as a fractional or percent value of the baseline $CO_2$ concentration.

Once the $CO_2$ concentration reaches the target level as set by the operator or physician, then the controller 230 commands the closure of the control valve 205 and the infant's lungs are again inflated to the preset super-atmospheric pressure (e.g. 30 cm $H_2O$). As soon as the inflation is complete, the controller 230 commands the control valve 205 to open to the atmosphere and commands the rapid inflation of the inflatable vest 220 by, for example, sending a signal to open the vest inflation valve 223 through the vest inflation signal line 237. Being rapidly inflated, the inflatable vest 220 compresses on the infant's thoracic-abdominal region and forces air in the infant's lungs to be exhaled. The flow of exhaled air is measured by the flow sensor 207. Once the forced expiratory maneuver is complete, as indicated by the cessation of expiratory flow through the flow sensor 207, the controller 230 commands the deflation of the inflatable vest 220 by opening the vest vent 225 through vent signal line 236 and closing the vest inflation valve 223 through the inflation valve signal line 237. The infant may then resume normal tidal breathing. During the inflation of the inflatable vest 220, the vest pressure may be constantly monitored by the vest pressure sensor 224, which transmits signals via the vest pressure sensor signal line 235 to the controller 230. The data collected relating to the flow rates of air in and out of the infant's lungs may be used to derive standard measures of pulmonary function such as the vital capacity, various measures of forced expiration rate, and the like.

In another embodiment, the apparatus 200 may also be operated in a semi-automated manner or manual operation whereby the operator controls the inflation and deflation of the infant's lungs and activates the inflatable vest 220 at the appropriate time when the $CO_2$ concentration has reached the desired level. In manual operation, for example, the operator would observe the signals from the flow sensor 207 as recorded and displayed on a display monitor and inflate and deflate the infant's lungs, for example, by placing his finger over the safety port 350 for inflation and removing his finger for deflation. In this example, the spring valve 320 and the exhaust port 330 are optionally deleted or closed. The operator would also observe the signals from the $CO_2$ sensor 208 and actuate a switch that will trigger the opening of the vest inflation valve 223 once the $CO_2$ concentration has reached the target level.

While preferred embodiments of the present invention have been shown and described, various modifications may be made without departing from the scope of the present invention. For example, while deflation of the infant's lungs has been described using a compression technique (e.g., through the use of an inflatable vest), it is also contemplated that deflation of the lungs can be performed by sucking the air from the infant's lungs using a negative pressure reservoir with a pressure set, for example, at minus 40 cm $H_2O$. The negative pressure reservoir can be in any form known in the art such as a regulatable vacuum source. In this embodiment, which may be used with intubated infants, the infant's lungs may be inflated and deflated with air for consecutive breathing cycles to a volume greater than the volume reached with the natural tidal inspiration as described above. When the $CO_2$ concentration has reached the target level, the infant's lungs are inflated once again to substantially total lung volume and immediately afterwards, the infant's lungs are deflated by connecting the negative pressure reservoir to the infant's airways, thereby sucking the air from the infant's lungs. This can be achieved by shunting the air flow from the lungs to the negative pressure reservoir by placing, for example, a switching type valve on the air conduct 204 in between the flow sensor 207 and the control valve 205 of FIG. 2 and connected to the negative pressure reservoir. The switching type valve (controlled by the controller 230 or the operator) can be switched, when deflation of the lungs is desired, so that air flow is closed to and from the control valve 205 and is opened only to the flow sensor 207, the $CO_2$ sensor 208, and ultimately the infant's lungs. When the flow of air coming from the infant's lungs ceases (as measured by zero expiratory flow), the switching type valve is switched back to the first position to resume regular breathing wherein the valve is closed to the negative pressure reservoir, but is opened to the control valve 205 and to the flow sensor 207, $CO_2$ sensor 208, and ultimately to the infant's lungs.

Moreover, while the air conduit 204 described above allows for inspired air and expired air to flow in the same passageway, it is also contemplated that in yet another embodiment of the invention, separate passages could be provided for inhaled air and exhaled air with the $CO_2$ sensor being located in the expiratory passage and the flow sensor having probes on each passage. Furthermore, the actual volume of air going in and out of the infant's lung can also be measured by an appropriate spirometer instead of, or in addition to, being calculated by integrating the flow rate signal from the flow sensor. Accordingly, the invention is not limited to the preferred embodiments described above but is only limited by the following claims and their equivalents.

The invention claimed is:

1. A method of performing a forced expiratory maneuver in an infant comprising the steps of:
    a) inflating the lungs of the infant with air synchronously with natural tidal inspiration to a lung volume greater than that reached at the end tidal inspiration for a plurality of consecutive respiratory cycles;
    b) monitoring end-tidal $CO_2$ concentration of the infant's respiration during each respiratory cycle;
    c) determining whether the end-tidal $CO_2$ concentration decreases from a baseline concentration by a pre-defined amount;
    d) inflating the infant's lungs to substantially total lung volume after a determination that the end-tidal $CO_2$ concentration decreases from the baseline concentration by the pre-defined amount; and
    e) immediately deflating the infant's lungs to produce a maximum forced expiration.

2. The method of claim 1 wherein the pre-defined amount ranges between 2 mmHg to 15 mmHg.

3. The method of claim 2 wherein the pre-defined amount ranges between 4 mmHg to 8 mmHg.

4. The method of claim 1 wherein the step of determining whether the end-tidal $CO_2$ concentration decreases from the baseline concentration is performed by a computer.

5. The method of claim 1 wherein the inflation of the infant's lungs to substantially total lung volume comprises the step of inflating the infant's lungs to a pressure of about 30 cm $H_2O$.

6. The method of claim 1 wherein said deflating step (e) is performed by compressing the infant's chest and abdomen with an inflatable vest.

7. The method of claim 1 wherein the deflating step (e) is performed by sucking the air out of the infant's lungs using a negative pressure reservoir.

8. A method of performing a forced expiratory maneuver in an infant comprising the steps of:
    a) inflating the lungs of the infant with air synchronously with natural tidal inspiration to a lung volume greater than that reached at the end tidal inspiration for a plurality of consecutive respiratory cycles;
    b) monitoring end-tidal $CO_2$ concentration of the infant's respiration during each respiratory cycle;
    c) determining whether the end-tidal $CO_2$ concentration decreases from a baseline concentration by a pre-defined amount;
    d) inflating the infant's lungs to substantially total lung volume after a determination that the end-tidal $CO_2$ concentration decreases from the baseline concentration by the pre-defined amount;
    e) immediately deflating the infant's lungs to produce a maximum forced expiration; and wherein steps (a)–(e) are performed by an apparatus in an automated manner.

9. An apparatus for performing a maximum forced expiration maneuver in an infant comprising:
    a mask connected to a source of breathable air that delivers the breathable air at super-atmospheric pressure;
    a flow sensor in fluid communication with the mask;
    a $CO_2$ sensor in fluid communication with the mask,
    an inflatable vest for compressing the infant's thoracic-abdominal region;
    a controller configured to receive a first signal from the flow sensor and a second signal from the $CO_2$ sensor and capable of commanding inflation of the infant's lungs and followed by inflation of the inflatable vest when the $CO_2$ sensor detects a $CO_2$ concentration equal to a target concentration of $CO_2$; and wherein the mask is connected to the source of breathable air via an air conduit comprising a control valve that is controlled by the controller and wherein super-atmospheric pressure is achieved when the control valve is closed.

10. An apparatus for performing a maximum forced expiration maneuver in an infant comprising:

a mask connected to a source of breathable air that delivers the breathable air at super-atmospheric pressure;

a flow sensor in fluid communication with the mask;

a $CO_2$ sensor in fluid communication with the mask, an inflatable vest for compressing the infant's thoracic-abdominal region;

a controller configured to receive a first signal from the flow sensor and a second signal from the $CO_2$ sensor and capable of commanding inflation of the infant's lungs and followed by inflation of the inflatable vest when the $CO_2$ sensor detects a $CO_2$ concentration equal to a target concentration of $CO_2$; and wherein the controller is an analog switching device.

11. An apparatus for performing a maximum forced expiration maneuver in an infant comprising:

a mask connected to a source of breathable air that delivers the breathable air at super-atmospheric pressure;

a flow sensor in fluid communication with the mask;

a $CO_2$ sensor in fluid communication with the mask, an inflatable vest for compressing the infant's thoracic-abdominal region;

a controller configured to receive a first signal from the flow sensor and a second signal from the $CO_2$ sensor and capable of commanding inflation of the infant's lungs and followed by inflation of the inflatable vest when the $CO_2$ sensor detects a $CO_2$ concentration equal to a target concentration of $CO_2$; and wherein the target concentration of $CO_2$ is a function of a baseline $CO_2$ concentration measured during the infant's natural tidal breathing derived by subtracting a pre-defined value from the baseline $CO_2$ concentration.

12. An apparatus for performing a maximum forced expiration maneuver in an infant comprising:

a mask connected to a source of breathable air that delivers the breathable air at super-atmospheric pressure;

a flow sensor in fluid communication with the mask;

a $CO_2$ sensor in fluid communication with the mask, an inflatable vest for compressing the infant's thoracic-abdominal region;

a controller configured to receive a first signal from the flow sensor and a second signal from the $CO_2$ sensor and cap able of commanding inflation of the infant's lungs and followed by inflation of the inflatable vest when the $CO_2$ sensor detects a $CO_2$ concentration equal to a target concentration of $CO_2$;

wherein the target concentration of $CO_2$ is a function of a baseline $CO_2$ concentration measured during the infant's natural tidal breathing;

wherein the target concentration of $CO_2$ is derived by subtracting a pre-defined value from the baseline $CO_2$ concentration; and the pre-defined value ranges between 2 mmHg to 15 mmHg.

* * * * *